US006947848B2

(12) United States Patent
Bove et al.

(10) Patent No.: US 6,947,848 B2
(45) Date of Patent: Sep. 20, 2005

(54) SYSTEM AND METHOD FOR IDENTIFYING UNKNOWN COMPOUNDS USING SPECTRA PATTERN RECOGNITION

(75) Inventors: John L. Bove, Ridgewood, NJ (US); Sheldon Walfish, Brooklyn, NY (US)

(73) Assignee: Cooper Union for the Advancement of Science and Art, New York, NY (US)

( * ) Notice: Subject to any disclaimer, the term of this patent is extended or adjusted under 35 U.S.C. 154(b) by 229 days.

(21) Appl. No.: 10/333,728

(22) PCT Filed: Aug. 3, 2001

(86) PCT No.: PCT/US01/24257

§ 371 (c)(1),
(2), (4) Date: Jun. 11, 2003

(87) PCT Pub. No.: WO02/12853

PCT Pub. Date: Feb. 14, 2002

(65) Prior Publication Data

US 2004/0024540 A1 Feb. 5, 2004

Related U.S. Application Data

(60) Provisional application No. 60/223,357, filed on Aug. 7, 2000.

(51) Int. Cl.[7] .............................................. G01N 31/00
(52) U.S. Cl. .................................... 702/27; 250/339.12
(58) Field of Search .............................. 702/19, 22–25, 702/27, 28, 30–32, 40, 49, 50, 134, 139, 140, 172; 250/256, 338.5, 339.12; 600/316

(56) References Cited

U.S. PATENT DOCUMENTS

| | | | |
|---|---|---|---|
| 3,711,764 A | 1/1973 | Ernst | 324/312 |
| 5,023,804 A | * 6/1991 | Hoult | 702/32 |
| 5,139,334 A | 8/1992 | Clarke | 356/301 |
| 5,252,829 A | * 10/1993 | Nygaard et al. | 250/339.09 |
| 5,266,800 A | * 11/1993 | Mullins | 250/256 |
| 5,448,070 A | * 9/1995 | Day et al. | 250/339.13 |
| 5,717,209 A | 2/1998 | Bigman et al. | 250/339.12 |
| 6,188,476 B1 | * 2/2001 | Hafeman et al. | 356/343 |

OTHER PUBLICATIONS

Witelski T et al., 1991 "An Application of Pattern Recognition and Infrared Spectroscopy To Water Analysis" *Intern. J. Environ. Anal Chem.* 44:127–136.

* cited by examiner

*Primary Examiner*—Marc S. Hoff
*Assistant Examiner*—Mohamed Charioui
(74) *Attorney, Agent, or Firm*—Goodwin Procter LLP

(57) ABSTRACT

A method of identifying and unknown compound comprises: (a) obtaining an absorption spectrum of the compound; (b) obtaining an absorbance value $A''(v_n)$ wherein $A''$ is the absorption value at a wavenumber $v_n$; (c) generating an array of values $A'''(v'_n)$ wherein $A'''(v'_n)=A'''(v'_n)-A''$ where $A''$ is an absorbance value which is modified from the measured absorbance, such as $A_{avg}$ where $A_{avg}$ is the average of $A''(v_n)$; (d) generating an array of values $I''(v_n)$ by integrating $A'''(v'_n)$ over a region of the spectrum; (e) normalizing the array of values $I''(v_n)$ with values $I'''(v'_n)$ obtained for a known compound. The system of this invention employs the above-described method in cooperation with a computer capable of receiving the absorption spectrum data and calculating values from the data using algorithms provided to the computer. The method and system of this invention may be used to identify unknown compounds for quality control, process control and other purposes.

16 Claims, 12 Drawing Sheets

Hexane Reference Spectrum

Integrated Reference Spectrum $I_R(v)$

Hexane Reference Spectrum

Combined Difference Spectrum
$R(v) = (I_S(v) - I_R(v)) / \text{rho}$

US 6,947,848 B2

SYSTEM AND METHOD FOR IDENTIFYING UNKNOWN COMPOUNDS USING SPECTRA PATTERN RECOGNITION

CROSS-REFERENCE TO RELATED APPLICATIONS

This is a national application for International Application No. PCT/US01/24257, which was filed on Aug. 3, 2001 and which published in English on Feb. 14, 2002, which in turn claims priority from U.S. Provisional Application Ser. No. 60/223,357, which was filed on Aug. 7, 2000.

BACKGROUND OF THE INVENTION

1. Field of the Invention

This invention is directed to a system and method for identifying an unknown compound using pattern recognition of spectra. More particularly, this invention is directed to a system and method for identifying an unknown compound using a spectrum pattern obtained from a spectrum such as an infrared absorption spectrum, and comparing the individual peak relationships in the spectrum pattern to the peak relationships in spectra patterns of known compounds to identify the unknown compound.

2. Background Information

Today the modern spectroscopist can enlist the valuable aid of a computer integrated with the analytical instrument of choice. This computer is used not only to help with the generation of the spectrum, but also with the identification of the spectrum produced. There is presently a growing interest to find new integrated methodologies to both collect and analyze spectral data. One such analytical technique is referred to as pattern recognition, which has been described further in the literature in, for example, J. Schurmann, *Pattern Classification: A Unified View, of Statistical and Neural Approaches* (John Wiley & Sons: New York, 1996); B. Ripley, *Pattern Recognition and Neural Networks* (Cambridge University Press: Cambridge, 1996); C. M. Bishop, *Neural Networks for Pattern Recognition* (Clarendon Press: Oxford, 1995); J. Wood, *Pattern Recognition*, Vol. 29 no. 1, pp. 1–17 (1996); Y. Smetanin, *Pattern Recognition and Image Analysis*, Vol. 5 no. 2, pp. 254–293 (1995); and the application of pattern recognition to the infrared analysis of water samples is described in T. Witelski et al., *Intent. J Environ. Anal. Chem.*, Vol. 44, pp. 127–136 (1990).

Computer based pattern and image recognition systems employing digital signal processing techniques have found many applications throughout science and industry. Typically, digital filters are custom designed for the particular application at hand, and are often computationally intensive. Disclosed herein is a system and method for identifying an unknown compound which employs a pattern matching technique that is flexible and computationally feasible, yet effective. Additionally, the present invention provides a useful form of visual feedback regarding the match between two patterns (referred to herein as waveforms, arrays, or spectra) that can be used to ascertain the nature of the difference between two waveforms.

In one preferred embodiment, the invention described herein employs infrared (IR) spectra. An important aid to chemists for the identification of organic compounds is the use of the infrared portion of the electromagnetic spectrum between 4000 cm$^{-1}$ and 400 cm$^{-1}$ (2.5–25 microns). It is well known that even the simplest of organic compounds is capable of generating a complex IR spectrum. These spectra are displayed as plots of percent transmittance vs. wavenumber, or as absorbence vs. wavenumber. For successful identification of a targeted compound, the sample in question should be relatively pure, and its spectrum adequately resolved and of reasonable intensity. The analyst must also use care to insure that the spectrophotometer is calibrated. Each compound's spectrum is generally unique, allowing the analyst to compare the unknown reagent to a reference compound.

The present invention employs a computer aided pattern recognition technique for analyzing the infrared spectra of organic compounds. Additionally, the technique is easily adapted to the analysis of different kinds of spectra produced by other instruments, such as a Raman spectrometer.

It is one object of this invention to provide a method of identifying unknown compounds using pattern recognition of spectra. It is another object of this invention to provide a system using a computer and pattern recognition of spectra to identify unknown compounds. Other objects, features and advantages of this invention will be apparent to those skilled in the art from the following detailed description of the invention.

SUMMARY OF THE INVENTION

This invention is directed to a method and system for identifying unknown compounds using spectra pattern recognition. The method comprises:

(a) obtaining an absorption spectrum of the compound of interest;

(b) obtaining an absorbance value $A''(v_n)$ wherein $A''$ is the absorption value at a wavenumber $v_n$;

(c) generating an array of values $A'''(v'_n)$ wherein $A'''(v'_n)=A''(v_n)-A''$ where $A''$ is an absorbance value which is modified from the measured absorbance, such as $A_{avg}$ where $A_{avg}$ is the average of $A''(v_n)$;

(d) generating an array of values $I''(v_n)$ by integrating $A'''(v'_n)$ over a region of the spectrum;

(e) normalizing the array of values $I''(v'_n)$ to obtain an array of values $I'''(v'_n)$; and (f) comparing the values $I'''(v'_n)$ with values $I'''_{std}(v'_n)$ obtained for a known compound.

The system comprises:

(a) providing a spectrometer capable of generating an absorption spectrum;

(b) providing a computer capable of receiving absorption spectrum data from the spectrometer and calculating values from the data using algorithms provided to the computer;

(c) obtaining an absorption spectrum of the compound of interest;

(d) obtaining an absorbance value $A''(v_n)$ wherein $A''$ is the absorption value at a wavenumber $v_n$;

(e) generating an array of values $A'''(v'_n)$ wherein $A'''(v'_n)=A''(v_n)-A''$ where $A''$ is an absorbance value which is modified from the measured absorbance, such as $A_{avg}$ where $A_{avg}$ is the average of $A''(v_n)$;

(f) generating an array of values $I''(v_n)$ by integrating $A'''(v'_n)$ over a region of the spectrum;

(g) normalizing the array of values $I''(v_n)$ to obtain an array of values $I'''(v'_n)$; and (h) comparing the values $1'''(v'_n)$ with values $I'''_{std}(v'_n)$ obtained for a known compound.

DETAILED DESCRIPTION OF THE INVENTION

Figure 1A:
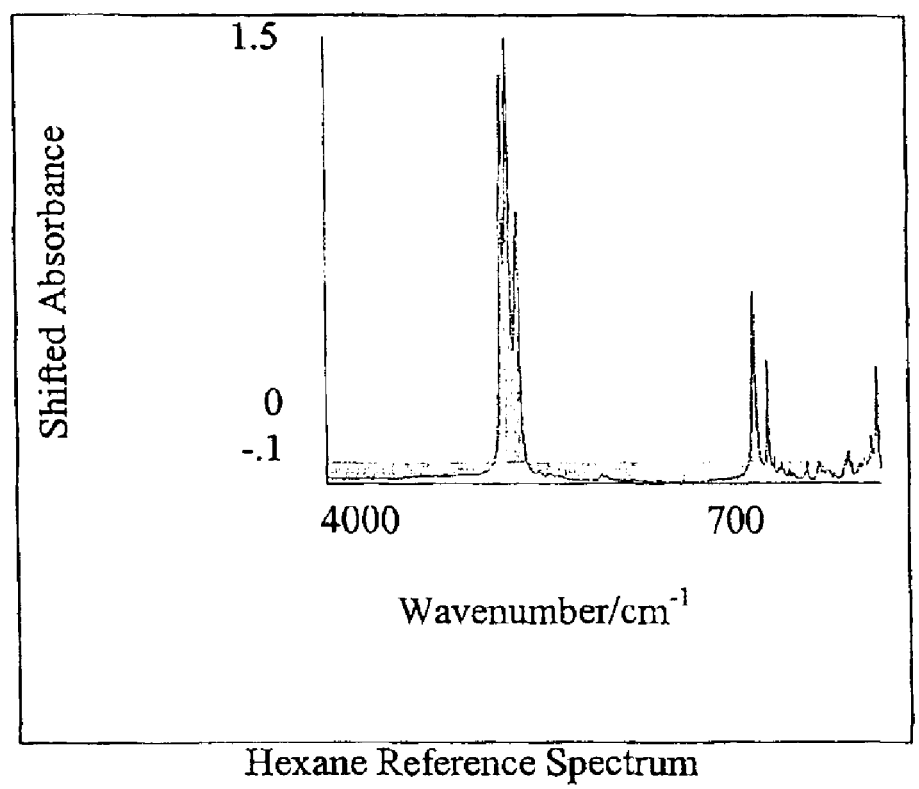
FIGS. 1A–1E depict various IR spectra for a hexane reference sample and a hexane test sample analyzed in accordance with this invention.
Figure 1B:
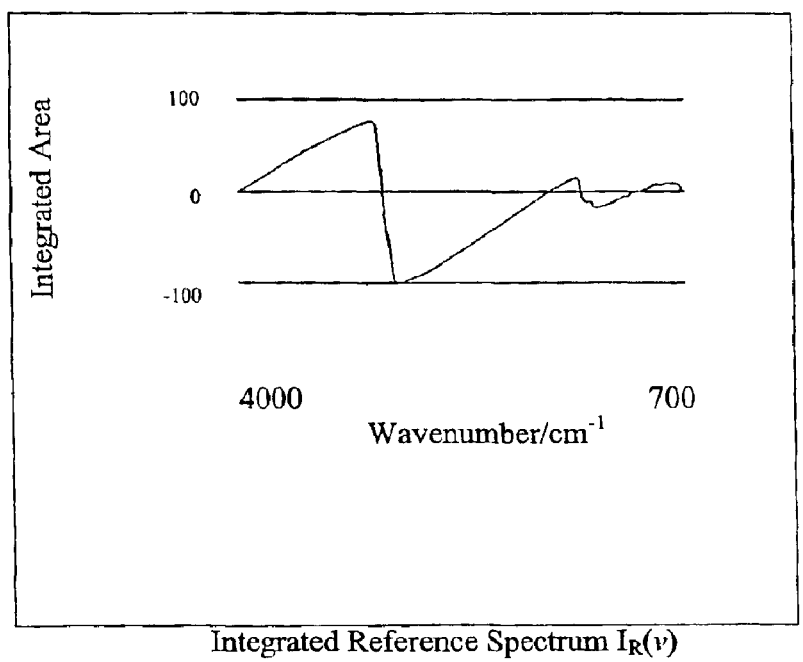
Figure 1C:
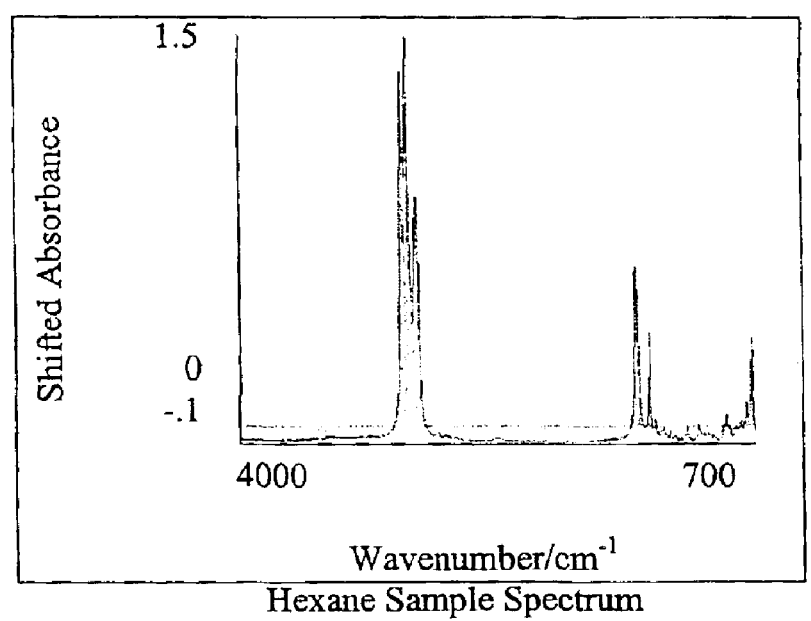
Figure 1D:
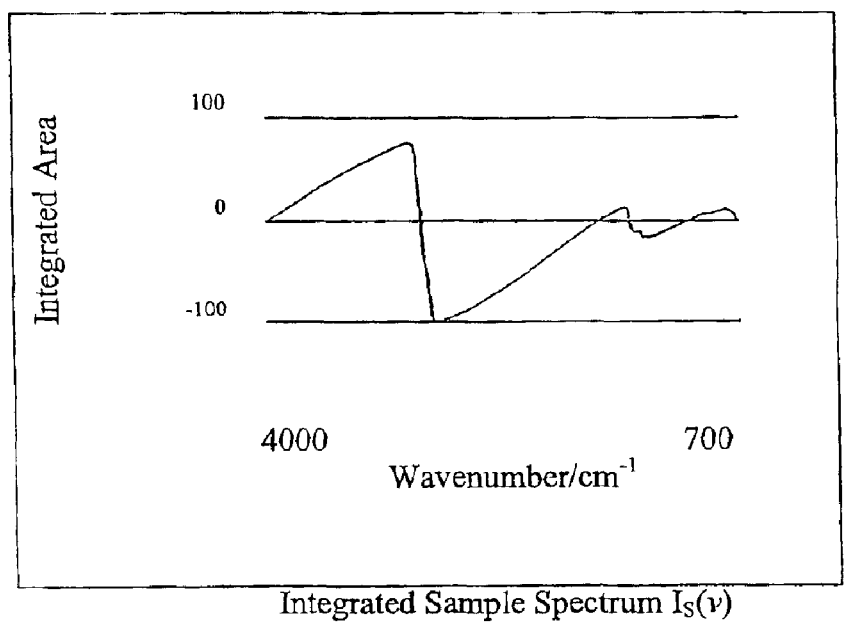
Figure 1E:
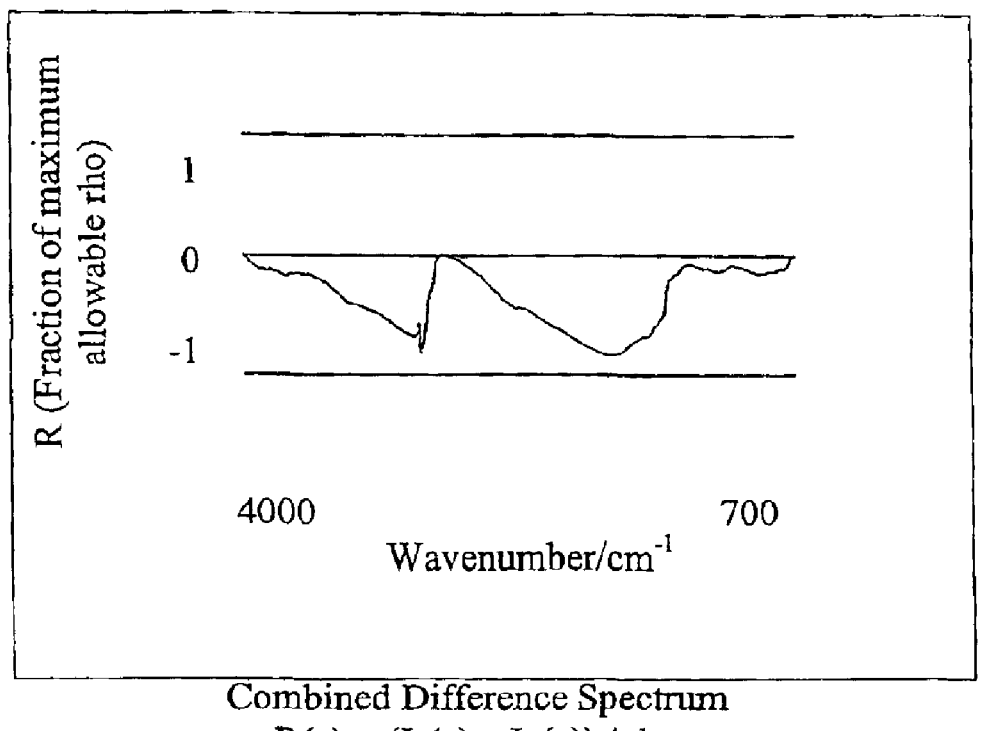

An infrared (IR) spectrum may be generated using a FT-IR spectrophotometer (represented by a plot of absorbance (A) vs. wavenumber (v) in cm$^{-1}$). An absorbance data array, A(v), is then produced by subtracting the average value from the original absorbance spectrum from equation (1):

$$A(v) = \text{Absorbance}(v) - A'' \tag{1}$$

A" is defined herein as an absorbance value which is modified from the measured absorbance A(v). For example, in a preferred embodiment A" may be the average value $A_{avg}$ of the measured absorbances. In yet another embodiment, A" may be proportional to $A_{avg}$. In yet another embodiment, A" is obtained by using baseline correction techniques to convert the measured absorbances to correct A" values.

The resulting absorbance spectrum (shifted along the vertical axis) is then normalized to a maximum absolute value using equation (2):

$$A'(v) = N A(v)/|A|_{max} \tag{2}$$

where $|A|_{max}$ is the maximum magnitude of the absorbance values A(v) obtained in equation (1) and N is a proportional factor, say 1.5.

This normalized array of absorbance vs. wavenumber is then used to generate a new function, representing the integral of the normalized absorbance using equation (3):

$$I(v) = \int_{700}^{v} A'(v')dv' \quad 700 \leq v \leq 4000 \tag{3}$$

Although an integration range of 700–4000 cm$^{-1}$ was used in one embodiment of this invention as set forth in equation (3), other convenient ranges may also be used. In a particularly preferred embodiment, the results can be improved dramatically by focusing the integration range on an appropriate region of the spectrum. For example, narrowing the range to 2800–3200 cm$^{-1}$ results in dramatically increased accuracy for identification of alkanes. A new data array I'(v') is then obtained from I(v) by multiplying by a factor of 100 and dividing through by $|I|_{max}$, i.e., by the maximum magnitude of I(v), as set forth in equation (4):

$$I'(v) = 100 I(v)/|I|_{max} \tag{4}$$

The values that result in the array are then used as a reference to compare with the I arrays of other spectra generated in a similar manner. This comparison is then used to determine whether a statistical match is produced. For purposes of experimental preference, a reference sample may be defined as the result of one generated spectrum or the average of several spectra. The reference I array may be labeled $I_R(v)$ and the test spectrum may be labeled $I_S(v)$. For purposes of comparison a rho array may then be derived as follows:

$$rho(v) = I_S(v) - I_R(v) \tag{5}$$

The largest member of the rho(v) array (absolute value) is selected as the minimum fitting tolerance rho, for which the sample data match the reference sample. In addition, a second test protocol may be used. In this case the variation between the two data sets are relative to a specifically selected maximum tolerance (as when testing for a match/no match case). An R(v) array may be produced which represents the amount of deviation from the reference spectrum as a fraction of the selected maximum tolerance. This methodology is summarized in equation (6):

$$R(v) = (I_S(v) - I_R(v))/rho \tag{6}$$

The resulting R(v) array may then be plotted against two parallel lines that are assigned values of −1 and 1 respectively. If all the values within the array lie between −1 and 1, the sample is accepted as a match to the reference sample. A non-match is defined as one in which any part of the spectrum differs by more than the rho assigned by the experimenter. This analysis is summarized in FIGS. 1 and 2.

The use of Fourier Transform (FT)-IR spectra was selected for the initial tests of the pattern matching technique. In this methodology the IR spectra generated and identification thereof were controlled from a personal computer. Spectra were generated using a Perkin-Elmer FT-IR 1600 Spectrophotometer possessing a resolution of 2 cm$^{-1}$. The sample compartment of the instrument was fitted with a Spectra-Tech Q-Circle cell, using an automated pump, which draws the sample into the cell, and which was later used to empty the sample cell. The cell was also fitted with a temperature control so that the temperature could be regulated. For the examples discussed herein, the cell temperature was maintained at 27° C. Whenever the cell was emptied, it was washed and flushed several times with an appropriate low boiling solvent (usually acetone), and then dried. The technique has also been used successfully with a diamond based ATR cell. The FT-IR and the Dell 486 Computer were integrated with an RS-232 cable.

Figure 2A:
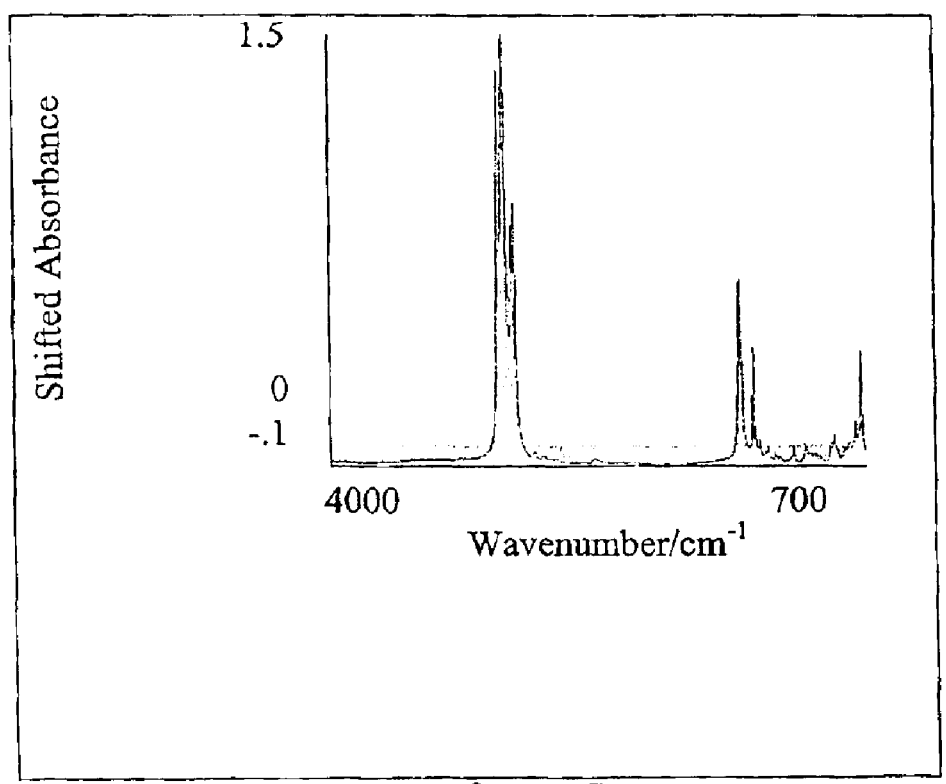
FIGS. 2A–2E depict various IR spectra for a hexane reference sample and a heptane test sample analyzed in accordance with this invention.
Figure 2B:
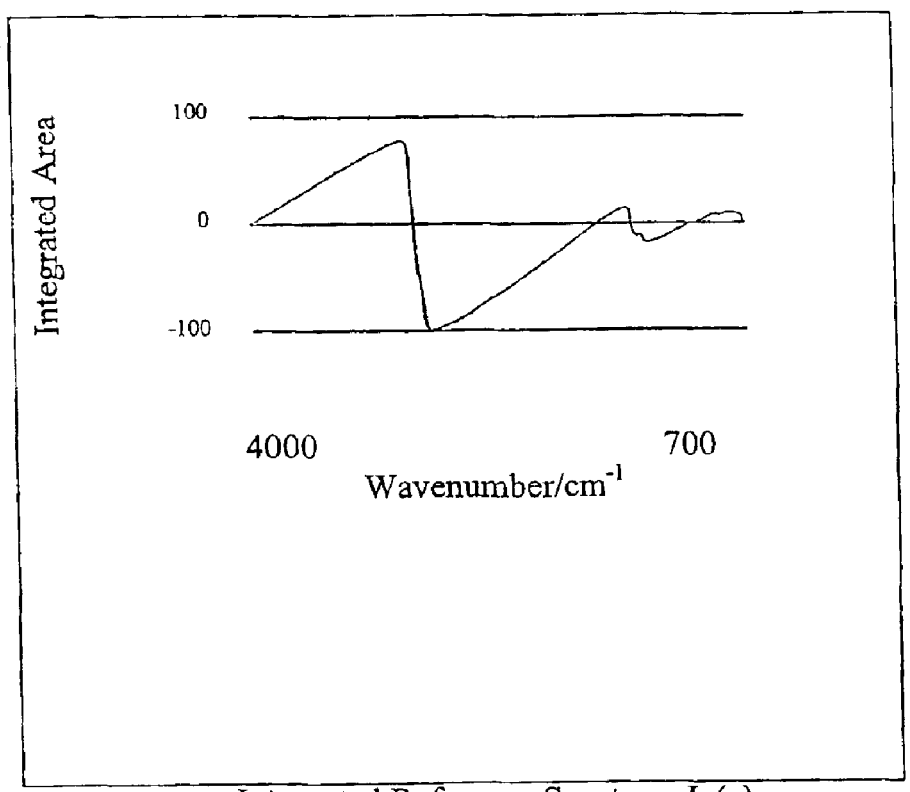
Figure 2C:
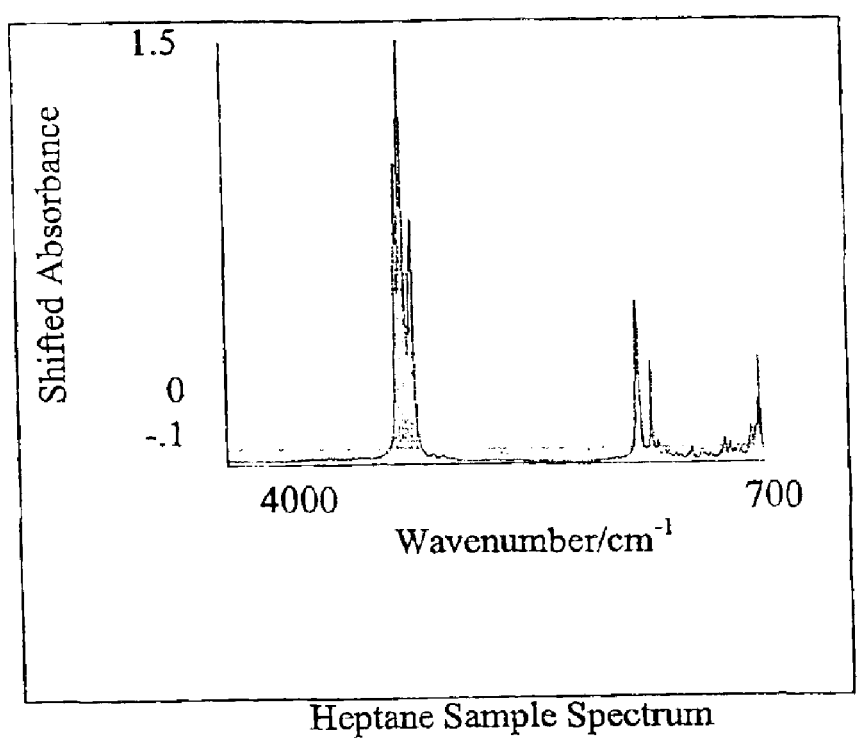
Figure 2D:
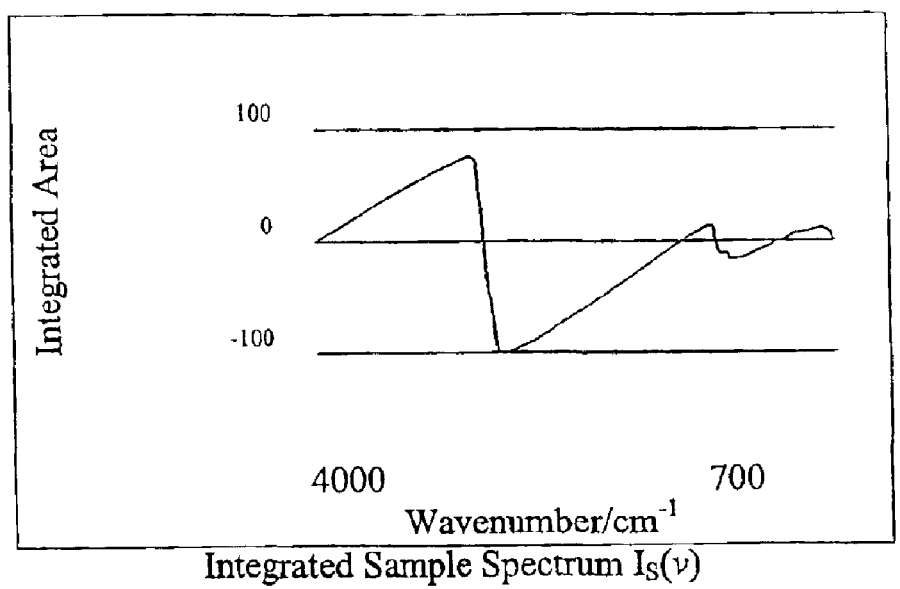
Figure 2E:
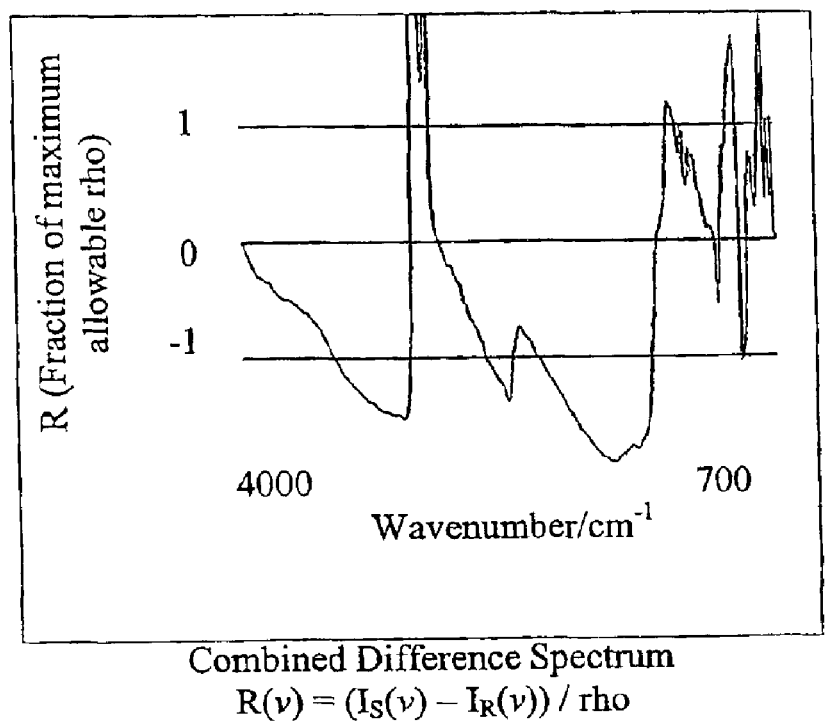

FIGS. 1A–1E depict the spectrum match of a hexane test sample vs. a hexane reference. It can be seen that in this case the rho tolerance has not been violated, and that the values remain within the two parallel lines in FIG. 1E. In the second case, illustrated in FIGS. 2A–2E, the spectrum match of a heptane test sample vs. a hexane reference is depicted. There should be no match between hexane and heptane; in fact, the rho tolerance between the two parallel lines in FIG. 2E has been exceeded in several places. In addition, it should be noted that this invention reveals where the violations occurred in the architecture of the IR spectrum, and that, this case, the location of the major difference was in the 3000 to 2800 cm$^{-1}$ region of the spectrum, as shown in FIG. 2E.

Thus, the largest value produced by equation (4) defines the maximum difference of any two points with the same wavenumber in the integral of the absorbance spectrum (normalized to 100). This fitting tolerance, rho, may then be compared to the fitting tolerances obtained by comparison with other reference spectra to determine a best fit. A smaller value of rho indicates a better match. It should be noted that at the edges of the spectrum, the rho sensitivity will be at a minimum. This occurs because the shape of the integral must converge to zero at these points.

It is well known in the field of infrared spectroscopy that alkane spectra possess just four major peaks: a C—H stretch at 3000 cm$^{-1}$, a $CH_2$ bending absorption at approximately 1465 cm$^{-1}$, a $CH_3$ bending absorption at approximately 1375 cm$^{-1}$, and a $CH_2$ bending (rocking) motion at approximately 720 cm$^{-1}$. Because of the similarity of the alkane spectra, it is difficult to identify alkanes without some supporting data such as boiling points or melting points. Accordingly, several alkanes along with a number of other organic functional groups were analyzed to demonstrate various embodiments of this invention and its computer-aided pattern recognition methodology. It has been found, for example, that the peaks associated with the C—H stretch at 3000 cm$^{-1}$ shift slightly with increasing carbon number. In fact, a linear relationship based on this sliding peak location among alkanes with carbon numbers from six to ten can be produced by using the pattern matching technique. It is expected that a mathematical relationship can be extended to higher numbered alkanes as well.

Figure 3:
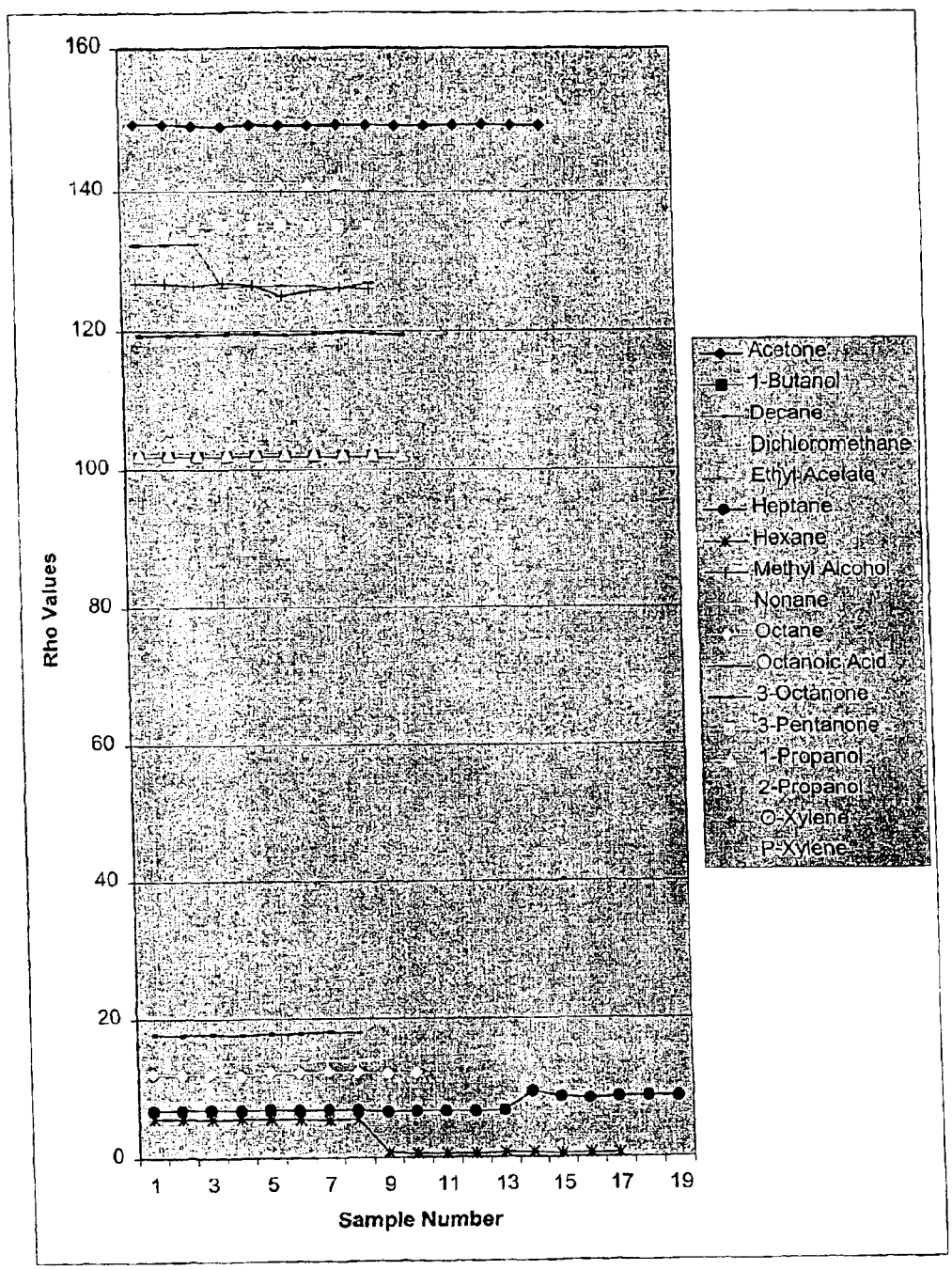
FIG. 3 depicts a summary of Rho values for various samples analyzed in accordance with this invention using a hexane reference.

Additional results were also obtained which indicated that the invention successfully selected and identified all subjected compounds when tested against a reference reagent. The alkane series was selected as the most challenging case. Hexane was selected as a reference example. The hexane reference IR spectrum was compared to several alkanes and to spectra belonging to a number of other functional groups. Use of this invention created no difficulty segregating the targeted reagents selected. For example, when the normalized average rho value of hexane was compared to that of heptane, octane, nonane, and decane, rho values of 2.56, 4.18, 4.83, and 6.13 respectively resulted. Other rho values for several other common functional groups are summarized along with the alkanes in Table 1 below and in FIG. 3. All of the groups tested far exceeded the rho values of the alkanes, providing additional support for the discrimination quality of the methodology employed in this invention.

TABLE 1

Summary of FT-IR Results

| Compound[a] | Trials | Rho (average) | Rho (S.D.) | Rho Normalized To Hexane Rho |
|---|---|---|---|---|
| Acetone | 15 | 149.401191 | 0.0914523 | 51.50117725 |
| 1-Butanol[b] | 9 | 101.9931618 | 0.0395431 | 35.15880876 |
| Decane | 8 | 17.79259485 | 0.1436879 | 6.133415503 |
| Dichloromethane[b] | 9 | 141.218456 | 0.1861294 | 48.68044682 |
| Ethyl Acetate[b] | 7 | 150.5074249 | 0.0335155 | 51.88251525 |
| Heptane | 19 | 7.416220192 | 0.9845838 | 2.556499504 |
| Hexane | 17 | 2.900927687 | 2.5250204 | 1 |
| Methyl Alcohol | 9 | 126.3112447 | 0.6006314 | 43.54167298 |
| Nonane | 9 | 14.00748805 | 0.2162604 | 4.828623656 |
| Octane | 10 | 12.13503435 | 0.1936251 | 4.183156446 |
| Octanoic Acid[b] | 9 | 128.4272765 | 2.9656636 | 44.27110579 |
| 3-Octanone[b] | 10 | 119.5266459 | 0.1336231 | 41.20290433 |
| 3-Pentanone[b] | 9 | 134.8421515 | 0.1632959 | 46.48242427 |
| 1-Propanol | 10 | 102.1891526 | 0.0624116 | 35.22637019 |
| 2-Propanol | 5 | 106.2541815 | 0.0479466 | 36.62765604 |
| P-Xylene[b] | 9 | 111.6938442 | 1.3170306 | 38.50280195 |
| O-Xylene[b] | 8 | 117.785263 | 0.1852507 | 40.60261947 |

[a]All compounds purchased from Aldrich Chemical Co. HPLC grade unless otherwise noted.
[b]Compound is 99% purity.

Figure 4:
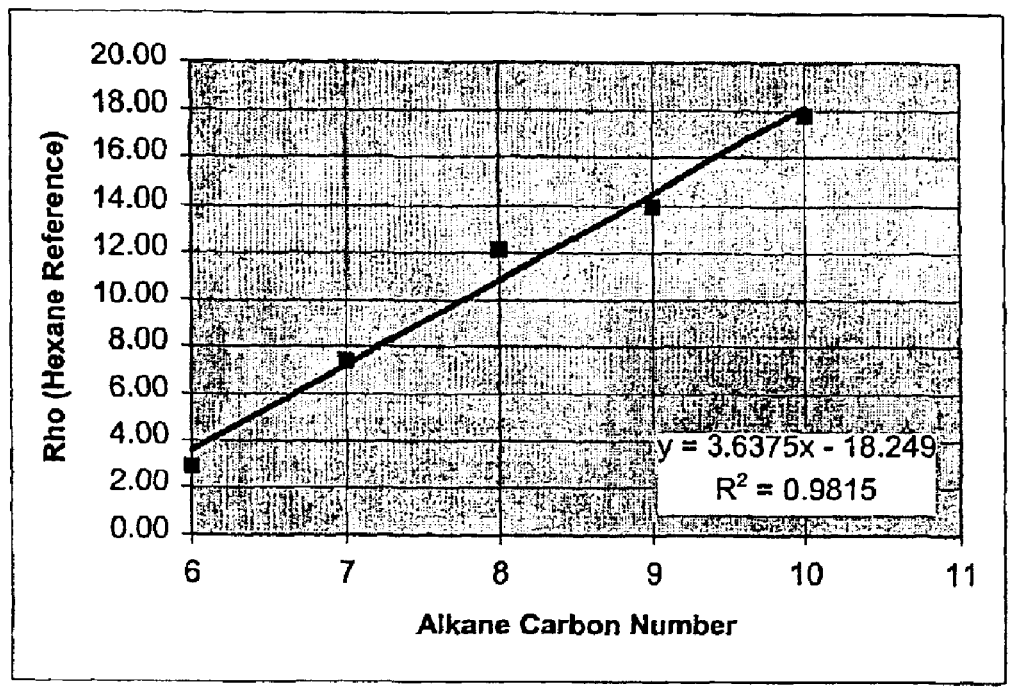
FIG. 4 depicts a linear fit of Rho values for a hexane reference sample vs. the alkane carbon number of alkane test samples.

A strong correlation was found to exist when the increasing rho value of a straight chain alkane was plotted against increasing carbon number. A linear relationship resulted with an R$^2$ value of 0.9815, as shown in FIG. 4. These results are similar to the well known plots of boiling points of a straight chain alkane homologous series against carbon number, as set forth, for example, at p. 141 of T. W. Solomons, *Organic Chemistry* (6th ed.) (John Wiley & Sons, N.Y. 1996). These homologs show a correlation between carbon number and boiling point. In the case of the carbon number versus boiling point, the relationship is attributed to van der Waals forces. With respect to the present invention, it was found that the rho difference in the general IR spectrum region of 3000 cm$^{-1}$ was the prime cause for this correlation.

In another embodiment of the system and method of this invention, proportional and derivative terms may be added to the integral, and possibly higher order integrals and derivatives as well. One example of such an embodiment is the following difference equation:

$$I(v)=C_I*A(v)+I(v-1)+C_P*(A(v)-A(v-1))+C_D*(A(v)-2*A(v-1)+A(v-2)) \quad (7)$$

The three constants, $C_I$, $C_P$, and $C_D$ represent "Integral," "Proportional," and "Derivative" terms, respectively, and must be chosen empirically to suit the particular instrument and process involved. It may also be possible to choose acceptable values for these constants through analytical means, although such an approach is likely to be more difficult. For example, a frequency analysis of the noise introduced by a given instrument might show that most of the noise is high frequency. In that case, it would be prudent to eliminate the derivative term, or minimize its impact by choosing zero or a small value for $C_D$. It is also important to choose an appropriate range for v, which will depend on the nature of the pattern match being sought, the instrument being used, and the particular waveform being examined. By specifying appropriate v ranges along with the waveforms in a library database, increased matching accuracy may be achieved.

More generally, this technique for processing an arbitrary waveform employs a method of normalization, typically involving subtraction of the mean value. A combination of integral, derivative, and proportional terms is then produced from the normalized spectrum. The integral, derivative, and proportional terms may be multiplied by constants, and some terms may be absent altogether. This newly produced data may then be used (optionally in combination with additional information such as the locations of peaks, peak area, and the length of the spectrum between two points) to assign a measure of degree of correlation between any number of waveforms. This correlation measurement may be assigned through the use of various techniques, such as finding the maximum absolute value of the difference between two processed waveforms, or taking a sum of squares of the difference between processed waveforms.

The pattern matching performed by this technique may be utilized to identify similarly shaped waveforms produced by any instrument, and preferably may be used in conjunction with IR and Raman spectroscopy for the easy identification of reagents, including organic compounds. It may be used to identify the best match, or a group of acceptable matches, from a database (or library) of known waveforms. It may also be used to determine how well two or more specified waveforms are matched to each other. Potential applications for this technique abound. Some of the possibilities include:

Identification of unknown reagents present in a reference library;
Identification of component groups in a reagent not present in the library;
Quality control of manufactured reagents.;
Process control of manufactured reagents;
Analysis of mixtures, including water mixtures (Raman spectroscopy is particularly well suited to this embodiment);
Analysis of drug content of bodily fluids (e.g. blood, urine, etc);
Analysis of sugar, etc. in blood;
Analysis of environmental contaminants; and
Authentication of paintings, money, etc.

It should be understood that various changes and modifications to the preferred embodiments described herein will be apparent to those skilled in the art. Such changes and modifications can be made without departing from the spirit and scope of this invention and without diminishing its attendant advantages. It is therefore intended that such changes and modifications be covered by the appended claims.

What is claimed is:

1. A system for identifying an unknown compound comprising:
   (a) providing a spectrometer capable of generating an absorption spectrum;
   (b) providing a computer capable of receiving absorption spectrum data from the spectrometer and calculating values from the data using algorithms provided to the computer;
   (c) obtaining an absorption spectrum of the compound;
   (d) obtaining an absorbance value $A^n(v_n)$ wherein $A^n$ is the absorption value at a wavenumber $v_n$;
   (e) generating an array of values $A'''(v'_n)$ wherein $A'''(v'_n) = A^n(v_n) - A''$ where $A''$ is a modified absorbance value of $A^n(v_n)$;
   (f) generating an array of values $I''(v_n)$ by integrating $A'''(v'_n)$ over a region of the spectrum;
   (g) normalizing the array of values $I''(v_n)$ to obtain an array of values $I'''(v'_n)$; and
   (h) comparing the values $I'''(v'_n)$ with values $I'''_{std}(v'_n)$ obtain for a known compound.

2. The system of claim 1, in which an infrared absorption spectrum of the compound is obtained, and $A^n$ is the infrared absorption value at a wavenumber $v_n$.

3. The system of claim 2, in which the absorption spectrum is obtained from an FT-IR spectrometer.

4. The system of claim 3, in which the absorption spectrum is obtained for the wavenumber range of 700 cm$^{-1}$ to 4000 cm$^{-1}$.

5. The system of claim 1, in which the absorption spectrum is obtained from a Raman spectrometer.

6. The system of claim 1, in which the absorption spectrum is obtained for an alkane compound.

7. The system of claim 1, in which $A'' = A_{avg}$.

8. A method of identifying an unknown compound comprising:
   (a) obtaining an absorption spectrum of the compound;
   (b) obtaining an absorbance value $A^n(v_n)$ wherein $A^n$ is the absorption value at a wavenumber $v_n$;
   (c) generating an array of values $A'''(v'_n)$ wherein $A'''(v'_n) = A^n(v_n) - A''$ where $A''$ is a modified absorbance value of $A^n(v_n)$;
   (d) generating an array of values $I''(v_n)$ by integrating $A'''(v'_n)$ over a region of the spectrum;
   (e) normalizing the array of values $I''(v_n)$ to obtain an array of values $I'''(v'_n)$; and
   (f) comparing the values $I'''(v'_n)$ with values $I'''_{std}(v'_n)$ obtained for a known compound.

9. The method of claim 8, in which an infrared absorption spectrum of the compound is obtained, and $A^n$ is the infrared absorption value at a wavenumber $v_n$.

10. The method of claim 9, in which the absorption spectrum is obtained from an FT-IR spectrometer.

11. The method of claim 8, in which the absorption spectrum is obtained for an alkane compound.

12. The method of claim 11, in which the absorption spectrum is obtained for the wavenumber range of 700 cm$^{-1}$ to 4000 cm$^{-1}$.

13. The method of claim 8, in which the absorption spectrum is obtained from a Raman spectrometer.

14. The method of claim 8, in which $A'' = A_{avg}$.

15. A method of identifying an unknown compound comprising:
   (a) obtaining an absorption spectrum of the compound;
   (b) obtaining an absorbance value $A^n(v_n)$ wherein $A^n$ is the absorption value at a wavenumber $v_n$;
   (c) generating an array of values $A'''(v'_n)$ wherein $A'''(v'_n) = A^n(v_n) - A''$ where $A''$ is a modified absorbance value of $A^n(v_n)$;
   (d) generating an array of values $I''(v_n)$ by integrating $A'''(v'_n)$ over a region of the spectrum where $I(v) = C_I * A(v) + I(v-1) + C_P*(A(v) - A(v-1)) + C_D*(A(v) - 2*A(v-1) + A(v-2))$ where $C_I$ is an integral constant, $C_P$ is a proportional constant and $C_D$ is a derivative constant obtained for the unknown compound;
   (e) normalizing the array of values $I''(v_n)$ to obtain an array of values $I'''(v'_n)$; and
   (f) comparing the values $I'''(v'_n)$ with values $I'''_{std}(v'_n)$ obtained for a known compound.

16. A system for identifying an unknown compound comprising:
   (a) providing a spectrometer capable of generating an absorption spectrum;
   (b) providing a computer capable of receiving absorption spectrum data from the spectrometer and calculating values from the data using algorithms provided to the computer;
   (c) obtaining an absorption spectrum of the compound;
   (d) obtaining an absorbance value $A^n(v_n)$ wherein $A^n$ is the absorption value at a wavenumber $v_n$;
   (e) generating an array of values $A'''(v'_n)$ wherein $A'''(v'_n) = A^n(v_n) - A''$ where $A''$ is a modified absorbance value of $A^n(v_n)$;
   (f) generating an array of values $I''(v_n)$ by integrating $A'''(v'_n)$ over a region of the spectrum where $I(v) = C_I * A(v) + I(v-1) + C_P*(A(v) - A(v-1)) + C_D*(A(v) - 2* A(v-1) + A(v-2))$ where $C_I$ is integral constant, $C_P$ is a proportional constant and $C_D$ is a derivative constant obtained for the unknown compound;
   (g) normalizing the array of values $I''(v_n)$ to obtain an array of values $I'''(v'_n)$; and
   (h) comparing the values $I'''(v'_n)$ with values $I'''_{std}(v'_n)$ obtained for a known compound.

* * * * *